United States Patent [19]

Joshua et al.

[11] Patent Number: 5,262,435
[45] Date of Patent: Nov. 16, 1993

[54] CHOLESTEROL LOWERING COMPOUNDS

[75] Inventors: Henry Joshua, Staten Island, N.Y.; Guy H. Harris, Cranford, N.J.

[73] Assignee: Merck & Co., Inc., Rahway, N.J.

[21] Appl. No.: 833,282

[22] Filed: Feb. 10, 1992

[51] Int. Cl.$^5$ .................. A61K 31/335; C07D 319/08
[52] U.S. Cl. ...................................... 514/452; 549/363
[58] Field of Search .......................... 549/363; 514/452

[56] References Cited

U.S. PATENT DOCUMENTS

| | | | |
|---|---|---|---|
| 5,026,554 | 6/1991 | Bartizal et al. | 549/363 |
| 5,053,425 | 10/1991 | Bartizal et al. | 514/452 |
| 5,055,487 | 6/1991 | Bartizal et al. | 514/452 |

FOREIGN PATENT DOCUMENTS

| | | |
|---|---|---|
| 0494622A1 | 7/1992 | European Pat. Off. |
| WO92/12156 | 7/1992 | PCT Int'l Appl. |
| WO92/12159 | 7/1992 | PCT Int'l Appl. |

OTHER PUBLICATIONS

Baxter et al, *Squalestatin 1, A Potent Inhibitor of Squalene Synthase Which Lowers Serum Cholesterol in Vivo, J. Biol. Chem.,* vol. 267, pp. 11705–11708 (1992).

*Primary Examiner*—Nicky Chan
*Attorney, Agent, or Firm*—Joseph F. DiPrima; Melvin Winokur

[57] ABSTRACT

A new Zaragozic acid analog has been isolated from a culture of MF5453. The compound and its derivatives are active as squalene synthetase inhibitors and are useful in the treatment of hypercholesterolemia.

15 Claims, No Drawings

CHOLESTEROL LOWERING COMPOUNDS

BACKGROUND OF THE INVENTION

Hypercholesterolemia is known to be one of the prime risk factors for isthemic cardiovascular disease, such as arteriosclerosis. Bile acid sequestrants have been used to treat this condition; they seem to be moderately effective but they must be consumed in large quantities, i.e. several grams at a time, and they are not very palatable.

MEVACOR ® (lovastatin), now commercially available, is one of a group of very active antihypercholesterolemic agents that function by limiting cholesterol biosynthesis by inhibiting the enzyme, HMG-CoA reductase.

Squalene synthetase is the enzyme involved in the first committed step of the de novo cholesterol biosynthetic pathway. This enzyme catalyzes the reductive dimerization of two molecules of farnesyl pyrophosphate to form squalene. The inhibition of this committed step to cholesterol should leave unhindered biosynthetic pathways to ubiquinone, dolichol and isopentenyl t-RNA.

Previous efforts at inhibiting squalene synthetase have employed pyrophosphate or pyrophosphate analog containing compounds such as those described in P. Ortiz de Montellano et al, J. Med Chem. 20, 243 (1977) and E. J. Corey and R. Volante, J. Am. Chem. Soc., 98, 1291 (1976). S. Biller (U.S. Pat. No. 4,871,721) describes isoprenoid (phosphinylmethyl)phosphonates as inhibitors of squalene synthetase.

Recently certain nonphosphorous containing inhibitors of squalene synthetase have been isolated as natural products. These natural product inhibitors are described in U.S. Pat. Nos. 5,053,425; 5,055,487 and 5,026,554.

U.S. Pat. No. 5,053,425 describes a squalene synthetase inhibitor of structure:

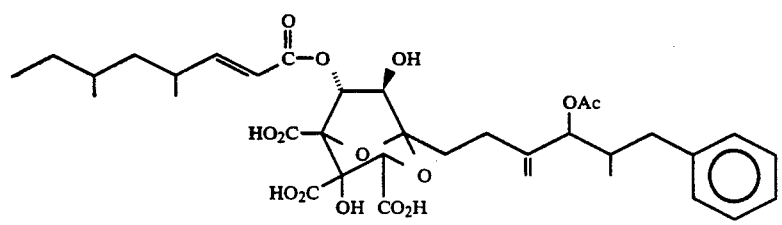

This compound was isolated from a fermentation broth employing a culture MF5453 (ATCC 20986).

The present invention relates to a novel compound which is structurally related to the above compound and which is useful as a squalene synthetase inhibitor and which has now been isolated from a MF5453 broth.

DETAILED DESCRIPTION OF THE INVENTION

The present invention is directed to novel compounds of structural formula (I) which are squalene synthetase inhibitors:

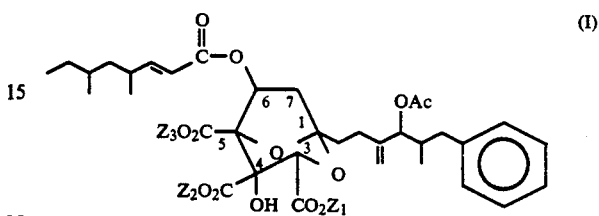

wherein $Z_1$, $Z_2$ and $Z_3$ are each independently selected from;
a) H;
b) $C_{1-5}$alkyl;
c) $C_{1-5}$alkyl substituted with a member of the group consisting of:
   i) phenyl,
   ii) phenyl substituted with methyl, methoxy, halogen (Cl, Br, I, F) or hydroxy; or
a pharmaceutically acceptable salt of a compound of of formula (I).

In one embodiment of the present invention are those compounds of formula (I) wherein the relative stereochemical configuration of the 2,8-dioxabicyclo[3.2.1]octane ring is as shown below:

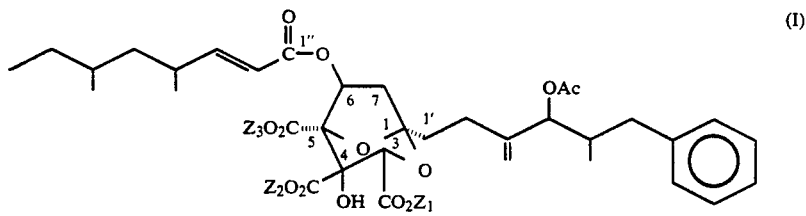

Throughout this specification and claims where stereochemistry is described for the dioxabicyclo[3.2.1]octane ring the configuration implied is relative. The actual configuration may be as shown or that of its enantiomer.

Further illustrating this embodiment are those compounds of structural formula (I) wherein the relative configuration at positions 3 and 6 is as shown below:

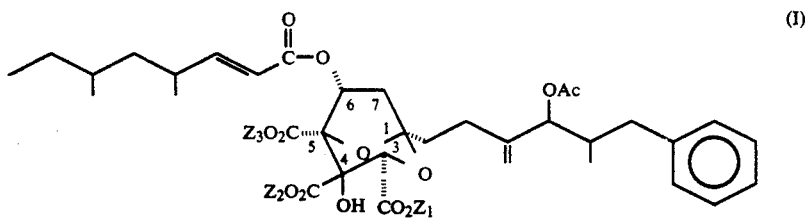

(I)

In one class of this embodiment are those compounds of structure (I) wherein the relative configuration at the 4-position is as shown below:

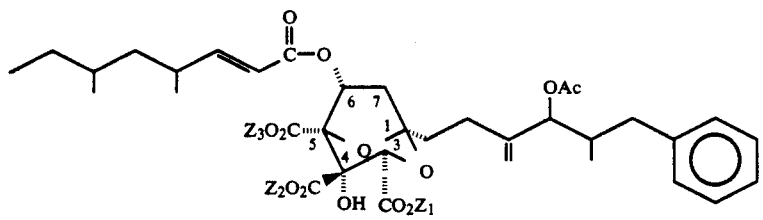

(I)

Exemplifying this class is the compound wherein $Z_1$, $Z_2$ and $Z_3$ are each hydrogen or a pharmaceutically acceptable salt thereof. The compound wherein $Z_1$, $Z_2$ and $Z_3$ are each hydrogen is hereafter referred to as compound A.

Further illustrating this class are those compounds in which one or more of $Z_1$, $Z_2$ or $Z_3$ is $C_{1-5}$alkyl or $C_{1-5}$alkyl substituted with phenyl or phenyl substituted with methyl, methoxy, halogen (Cl, Be, I, F) or hydroxy.

The compounds of formula (I) are prepared in an aerobic fermentation procedure employing a culture, MF5453, observed as a sterile mycelium. Mutants of MF5453 are also capable of producing compounds of this invention, and are included within the scope of this invention. Such mutants have essentially the same characteristics as those described for MF5453.

The culture MF5453 is that of a fungus isolated from a water sample obtained from the Jalon river, Zaragoza, Spain. This culture has been deposited with the American Type Culture Collection at 12301 Parklawn Drive, Rockville, Md. 20852 as ATCC 20986.

The microorganism MF5453, its morphological characteristics and a fermentation procedure using this microorganism has been described in U.S. Pat. No. 4,053,425.

Compounds of this invention can be obtained by culturing the above noted microorganism in an aqueous nutrient medium containing sources of assimilable carbon and nitrogen, preferably under aerobic conditions. Nutrient media may also contain mineral salts and defoaming agents.

The preferred sources of carbon in the nutrient medium are carbohydrates such as glucose, glycerin, starch, dextrin, and the like. Other sources which may be included are maltose, mannose, sucrose, and the like. In addition, complex nutrient sources such as oat flour, corn meal, millet, corn and the like may supply utilizable carbon. The exact quantity of the carbon source which is used in the medium will depend, in part, upon the other ingredients in the medium, but is usually found in an amount ranging between 0.5 and 5 percent by weight. These carbon sources can be used individually in a given medium or several sources in combination in the same medium.

The preferred sources of nitrogen are amino acids such as glycine, methionine, proline, threonine and the like, as well as complex sources such as yeast extracts (hydrolysates, autolysates), dried yeast, tomato paste, soybean meal, peptone, corn steep liquor, distillers solubles, malt extracts and the like. Inorganic nitrogen sources such as ammonium salts (e.g. ammonium nitrate, ammonium sulfate, ammonium phosphate, etc.) can also be used. The various sources of nitrogen can be used alone or in combination in amounts ranging between 0.2 to 70 percent by weight of the medium.

The carbon and nitrogen sources are generally employed in combination, but need not be in pure form. Less pure materials which contain traces of growth factors, vitamins, and mineral nutrients may also be used. Mineral salts may also be added to the medium such as (but not limited to) calcium carbonate, sodium or potassium phosphate, sodium or potassium chloride, magnesium salts, copper salts, cobalt salt and the like. Also included are trace metals such as manganese, iron, molybdenum, zinc, and the like. In addition, if necessary, a defoaming agent such as polyethylene glycol or silicone may be added, especially if the culture medium foams seriously.

The preferred process for production of compounds of this invention consists of inoculating spores or mycelia of the producing organism into a suitable medium and then cultivating under aerobic condition.

The fermentation procedure generally is to first inoculate a preserved source of culture into a nutrient seed medium and to obtain, sometimes through a two step process, growth of the organisms which serve as seeds in the production of the active compounds. After inoculation, the flasks are incubated with agitation at temperatures ranging from 20° to 30° C., preferably 25° to 28° C. Agitation rates may range up to 400 rpm, preferably 200 to 220 rpm. Seed flasks are incubated over a period of 2 to 10 days, preferably 2 to 4 days. When growth is plentiful, usually 2 to 4 days, the culture may be used to inoculate production medium flasks. A second stage seed growth may be employed, particularly when going into larger vessels. When this is done, a portion of the culture growth is used to inoculate a second seed flask incubated under similar condition but employing shorter time.

After inoculation, the fermentation production medium is incubated for 3 to 30 days, preferably 14 to 21 days, with or without agitation (depending on whether liquid or solid fermentation media are employed). The fermentation is conducted aerobically at temperatures ranging from 20° to 40° C. If used, agitation may be at a rate of 200 to 400 rpm. To obtain optimum results, the temperatures are in the range of 22° to 28° C., most preferably 24° to 26° C. The pH of the nutrient medium suitable for producing the active compounds is in the range of 3.55 to 8.5, most preferably 5.0 to 7.5. After the appropriate period for production of the desired compound, fermentation flasks are harvested and the active compound isolated.

The pH of the aqueous mycelial fermentation is adjusted to between 1 and 9 (preferably between 3 and 5). The aqueous mycelial fermentation is preferably mixed with a water miscible solvent such as methanol and the mycelia filtered. The active compound may then be isolated from the aqueous filtrate by several methods including:

1. Liquid-liquid extraction of the aqueous filtrate into a water immiscible solvent such as methyl ethyl ketone, ethyl acetate, diethyl ether, or dichloromethane preferably after having adjusted the pH to between 3 and 5.

2. Solid-liquid extraction of the aqueous filtrate onto an organic matrix such as SP207 or HP-20 and elution with an organic solvent (aqueous or nonaqueous) such as 90/10 methanol/water or 90/10 acetone/water.

3. Adsorption of the active compound from the aqueous filtrate onto an ionic exchange resin such as Dowex 1($Cl^-$) or Dowex 50 ($Ca^{2+}$) and elution with a high ionic strength organic/aqueous solvent such as 90/10 methanol/aqueous 30% $NH_4C$. This material could then be desalted by employing either method 1 or 2 above. Each of these three methods may also be used in the further purification of the active compound.

The fraction containing active compound from the above methods could then be dried in vacuo leaving the crude active compound. The crude active compound is then generally subjected to several separation steps such as adsorption and partition chromatography, and precipitation. For each separation step, fractions are collected and combined based on results from a bioassay and/or HPLC analysis.

The chromatographic separations may be carried out by employing conventional column chromatography with ionic or nonionic adsorbent. When silica gel is the adsorbent, an alcohol/chlorohydrocarbon/organic acid mixture such as methanol/chloroform/acetic acid/water is useful as an eluant. For reverse phase chromatography, the preferred adsorbent is a C18 or C8 bonded phase silica gel. The preferred eluant for reverse phase chromatography is a mixture of acetonitrile and water buffered at a low pH, such as with 0.1% phosphoric acid, or trifluoroacetic acid. The active compound can be precipitated out of a non-polar solvent as the quinine salt. The preferred solvent for precipitation is diethyl ether.

The present invention is also directed to a method of inhibiting cholesterol biosynthesis which comprises the administration to a subject in need of such treatment a nontoxic therapeutically effective amount of a compound represented by structural formula (I) and pharmaceutically acceptable salts thereof. Specifically, the compounds of this invention inhibit the enzyme squalene synthetase and are useful as antihypercholesterolemic agents for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 20 mg to 2000 mg (preferably 20 to 100 mg) which may be given in two to four divided doses. Higher doses may be favorably employed as required.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glucamine, lysine, arginine, ornithine, choline, N,N'-dibenzylethylene-diamine, chloroprocaine, diethanolamine, procaine, N-benzylphenethylamine, diethylamine, piperazine, tris(hydroxymethyl)aminomethane, and tetramethylammonium hydroxide. This invention includes salts of one, two or three of the carboxyl groups of formula (I).

The compounds of this invention may also be administered in combination with other cholesterol lowering agents such as those which inhibit an enzymatic pathway in the biosynthesis of cholesterol. Example of such agents would include but are not limited to HMG-CoA reductase inhibitors, HMG-CoA synthase inhibitors, and squalene expoxidase inhibitors. Illustrative of such inhibitors are lovastatin, simvastatin, pravastatin and fluvastatin. Other cholesterol lowering agents that may be administered include niacin, probucol, and the fibric acids, clofibrate and gemfibrozil. Appropriate daily dosages for adults are niacin (2-8 gm), probucol (up to 1000 mg), clofibrate (up to 2 gm) and gemfibrozil (800-1500 mg).

The compounds of this invention may also be coadministered with pharmaceutically acceptable nontoxic cationic polymers capable of binding bile acids in a non-reabsorbable form in the gastro-intestinal tract. Examples of such polymers include cholestyramine, colestipol and poly[methyl-(3-trimethylaminopropyl-)imino-trimethylene dihalide]. The relative amounts of the compounds of this invention and these polymers is between 1:100 and 1:15,000.

The intrinsic squalene synthetase inhibitory activity of representative compounds of this invention was measured by the standard in vitro protocol described below:

Preparation of Microsomes

Male, Charles River CD rats (120 to 150 g) were fed a diet containing 0.1% lovastatin for 4 days. The livers from these rats were homogenized in 5 volumes (ml/g) of ice cold 50 Mm HEPES (4-(2-hydroxyethyl)-1-piperazine-ethanesulfonic acid), 5 mM EDTA(ethylenediaminetetraacetic acid) pH 7.5 with a Potter-Elvehjem type tissue grinder. The homogenate was centrifuged twice at 20,000×g for 15 minutes at 4,C, discarding the pellet each time. The supernatant was then centrifuged at 100,000×g for 1 hour at 4° C. The resulting microsomal pellet was resuspended in a volume of the above homogenizing buffer equal to one-fifth the volume of the original homogenate. This microsomal preparation has a protein concentration of about 7 mg/ml. The microsomal suspensions were stored in aliquots at −70° C. Squalene synthetase activity in these aliquots is stable for at least several months.

Partial Purification of Prenyl Transferase

Prenyl transferase was purified to use in the enzymatic synthesis of radiolabelled farnesyl pyrophosphate. Prenyl transferase was assayed by the method of Rilling (Methods in Enzymology 110, 125-129 (1985)) and a unit of activity is defined as the amount of enzyme that will produce 1 μmole of farnesyl pyrophosphate per minute at 30° C. in the standard assay.

The livers of 23 forty-day old male rats that had been fed 5% cholestyramine plus 0.1% lovastatin were homogenized in a Waring blender in 1 liter of 10 mM mercaptoethanol, 2 mM EDTA, 25 μM leupeptin, 0.005% phenylmethyl sulfonyl fluoride pH 7.0 containing 0.1 trypsin inhibitor units of aprotinin/ml. The homogenate was centrifuged at 20,000×g for 20 minutes. The supernatant was adjusted to pH 5.5. with 6N HOAc and centrifuged at 100,000×g for 1 hour. This supernatant was adjusted to pH 7.0 with 3N KOH and a 35-60% ammonium sulfate fraction taken. The 60% pellet was redissolved in 60 ml of 10 mM potassium phosphate, 10 mM mercaptoethanol, 1 mM EDTA pH 7.0 (Buffer A) and dialyzed against two 1 liter changes of Buffer A. This dialyzed fraction was applied to a 12.5×5 cm column of DEAE-sepharose 4B equilibrated with Buffer A. The column was washed with 700 ml of Buffer A and a 1 liter gradient from Buffer A to 100 mM potassium phosphate, 10 mM mercaptoethanol, 1 mM EDTA pH 7.0. Fractions having a specific activity greater than 0.20 units/mg were combined, solid ammonium sulfate was added to bring to 60% saturation and pelleted. The pellet was dissolved in 8 ml of 10 mM Tris, 10 mM β-mercaptoethanol pH 7.0 (Buffer B). The redissolved pellet was taken to 60% saturation with ammonium sulfate by adding 1.5 volumes of saturated ammonium sulfate in Buffer B. This ammonium sulfate suspension contained 3.5 units/ml with a specific activity of 0.23 units/mg and was free of isopentenyl pyrophosphate isomerase activity. This ammonium sulfate suspension was used for the synthesis of [4-$^{14}$C]farnesyl-pyrophosphate and its activity was stable stored at 4° C. for at least 6 months.

Enzymatic Synthesis of [4-$^{14}$C]farnesyl-pyrophosphate

The solvent (ethanol: 0.15 N NH$_4$OH, 1:1) was removed from 55 μCi of [4-$^{14}$C]isopentenyl pyrophosphate (47.9 [μCi/[μmole]) by rotary evaporation. Six hundred microliters of 100 mM Tris, 10 mM MgCl$_2$, 4 mM dithiothreitol pH 7.5 was added and the solution was transferred to a 1.5 ml Eppendorf centrifuge tube. Geranyl-pyrophosphate, 250 μl of a 20 mM solution, and 50 μl of the ammonium sulfate suspension of prenyl transferase were added to initiate the reaction. This incubation contained 5 μmoles of geranyl pyrophosphate, 1.15 μmoles of isopentenyl pyrophosphate, 6 μmoles of MgCl$_2$ and 0.18 units of prenyl transferase in a volume of 900 μl. The incubation was conducted at 37° C. During the incubation, the mix turned cloudy white as the newly formed magnesium complex of farnesyl pyrophoshate precipitated out of solution. The [4-$^{14}$C]farnesyl pyrophosphate was collected by centrifugation for 3 minutes at 14,000 rpm in an Eppendorf centrifuge tube, the supernatant removed, and the pellet was dissolved in 1.0 ml of 50 mM HEPES, 5 mM EDTA, pH 7.5 The yield was 50.7 μCi (92%) of [4-$^{14}$C]farnesyl pyrophosphate. The (4-$^{14}$C]farnesyl pyrophosphate was stored in aliquots at −70° C.

Squalene Synthetase Assay

Reaction were performed in 16×125 mm screw cap test tubes. A batch assay mix was prepared from the following solution:

|  | μl per assay | volume for 50 assays |
|---|---|---|
| 1. 250 mM Hepes pH 7.5 | 20 | 1000 |
| 2. NaF 110 mM | 10 | 500 |
| 3. MgCl$_2$ 55 mM | 10 | 500 |
| 4. Dithiothreitol 30 mM | 10 | 500 |
| 5. NADPH 10 mM (made fresh) | 10 | 500 |
| 6. [4-$^{14}$C]farnesyl-pyrophosphate 47.9 μCi/μmole, and 0.025 μCi/3.0 μl | 3.0 | 150 |
| 7. H$_2$O | 24 | 1200 |

This assay mix was degassed under a vacuum and flushed with N$_2$. Solutions of the squalene synthetase inhibitors were prepared either in DMSO or MeOH and a 1:120 dilution of the microsomal protein was made with the original homogenizing buffer. For each reaction, 87 μl of the assay mix was taken with 3 μl of an inhibitor solution (DMSO or MeOH in the controls), warmed to 30° C. in a water bath and then the reaction was initiated by the additon of 10 μl of the 1:120 dilution of microsomal protein (0.6 μg protein total in the assay). The reactions were stopped after 20 minutes by the addition of 100 μl of a 1:1 mix of 40% KOH with 95% EtOH. The stopped mix was heated at 65° C. for 30 minutes, cooled, 10 ml of heptane was added and the mix was vortexed. Two g of activated alumina was then added, the mix vortexed again, the alumina allowed to settle and 5 ml of the heptane layer was removed. Ten ml of scintillation fluid was added to the heptane solution and radioactivity was determined by liquid scintillation counting.

Percent inhibition is calulated by the formula:

$$1 - \frac{[\text{Sample} - \text{Blank}]}{[\text{Control} - \text{Blank}]} \times 100$$

IC$_{50}$ values were determined by plotting the log of the concentration of the test compound versus the percentage inhibition. The IC$_{50}$ is the concentration of inhibitor that give 50% inhibition as determined from these plots.

Compound A of this invention exhibited an IC$_{50}$ value of 0.950 nM.

The present compounds also demonstrate broad spectrum antifungal activity as determined by broth or agar dilution methods. Thus the present invention is also directed to a method of treating fungus infections which comprises the administration to an organism in need of such treatment of a nontoxic therapeutically effective amount of a compound represented by the structural formula (I) and pharmaceutically acceptable salts thereof. Generally from 2 to about 20 mg/kg should be employed as a unit dosage in an antifungal treatment.

Furthermore, the compounds of the present invention have been found to be inhibitors of farnesyl-protein transferase and thereby of farnesylation of the RAS protein and thus block the ability of RAS to transform normal cells to cancer cells. Farnesyl-protein transferase activity may be reduced or completely inhibited by adjusting the compound dose.

The intrinsic farnesyl-protein transferase (FTase) activity of representative compounds of this invention is measured by the assays described below:

RASIT ASSAY I

Farnesyl-protein transferase (FTase) from bovine brain is chromatographed on DEAE-Sephacel (Pharmacia, 0–0.8 M NaCl gradient elution), N-octyl agarose (Sigma, 0–0.6 M Nacl gradient elution), and a mono Q HPLC column (Pharmacia, 0–0.3 M NaCl gradient). Ras-CVLS at 3.5 $\mu$M, 0.25 $\mu$M [$^3$H]FPP, and the indicated compounds are incubated with this partially purified enzyme preparation.

RASIT ASSAY II

Farnesyl-protein transferase (Ftase) from bovine brain was chromatographed on DEAE-Sephacel (Pharmacia, 0–0.8 M NaCl gradient elution), N-octyl agarose (Sigma, 0–0.6 M Nacl gradient elution), and a mono Q HPLC column (Pharmacia, 0–0.3 M NaCl gradient). Ras-CVLS at 1.0 $\mu$M, 0.5 $\mu$M [$^3$H]FPP, and the indicated compounds were incubated with this partially purified enzyme preparation. The Ftase data is a measurement of the ability of the test compound to inhibit Ras farnesylation in vitro.

The pharmaceutical compositions containing the compounds of structural formula I inhibit farnesyl-protein transferase and the farnesylation of the oncogene protein Ras. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The present invention also encompasses a method of the treatment of cancer, comprising the administration of a pharmaceutical composition comprising a therapeutically effective amount of the compounds of this invention, with or without pharmaceutically acceptable carriers or diluents.

Suitable compositions of this invention include aqueous solutions comprising compounds of this invention and pharmacologically acceptable carrier, e.g. saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a human patient undergoing treatment for cancer. Administration occurs in an amount between about 0.1 mg/kg of body weight to about 20 mg/kg of body weight of a mammal per day, preferably of between 0.5 mg/kg of body weight to about 10 mg/kg of body weight of a mammal a day.

The following examples illustrate the preparation of the compounds of formula (I) and their incorporation into pharmaceutical compositions and as such are not to be considered as limiting the invention set forth in the claims appended hereto.

EXAMPLE 1

Preparation of Compound A

A. Cultivating MF5453

Culture 5453 was grown through four seed stages at 25° C. in a medium of the following composition per liter: corn steep liquor, 5 g; glucose, 10 g; tomato paste, 40 g; oat flour, 10 g. A 400 liter sample from the fourth stage was used to inoculate 11,000 liters of production medium of the following composition per liter: malt extract, 15 g; glucose, 55 g; Hysoy peptone, 10 g; KH$_2$PO$_4$, 3 g; MgSO$_4$·7H$_2$O, 1.5 g. The fermentation was run at 25° C. for 385 hours whereupon a total of 9300 liters of broth was harvested.

B. Extraction

The whole broth from above was adjusted to PH=4.1 with H$_2$SO$_4$, 9300 liters of methanol were added and the mixture stirred overnight. The solids were removed using a Westfalia decanter. The resulting supernatant A of 16,086 liters was discarded. The dewatered solids were re-extracted with 79% methanol/H$_2$O as above, the solids were removed using a Westfalia decanter and a supernatant B of 6,813 liters was collected.

C. Isolation

Supernatant B from above was adjusted to 50% methanol/50% H$_2$O and loaded onto a 500 liter column of Mitsubishi SP-207 resin at 4 gal/min. The column was then washed with 2,000 liters of 60% methanol/40% H$_2$O at 4 gal/min. followed by elution with 90% methanol/10% H$_2$O at 4 gal/min., collecting 50 gal fractions. Fractions 3–20 were pooled and adjusted to 40% H$_2$O. The solution was processed in two portions. Each portion was loaded onto a 100 liter column of Diaion HP-20 at 0.6 gal/min. The HP-20 column was washed with 400 liters 60% methanol/40% H$_2$O at 0.6 gal/min. and then eluted with 100% methanol at 0.6 gal/min. collecting 15 gal fractions. Fractions 2–4 from each column were pooled and concentrated at 40° C. in vacuo to a final volume of 57 liters.

2.78 liters from the above volume of 57 liters were adjusted to 66% methanol and 60 Mm sodium formate at pH=4.5. This solution was loaded onto a column of BioRad AG4×4 (V$_b$=440 ml, 100–200 mesh, formate cycle) which had been equilibrated with 4 column volumes of 60% methanol/40% 0.1 M formic acid adjusted to pH=4.4 with NaOH. The column was washed with 1800 ml of equilibration buffer and 2000 ml of a solution of 60% CH$_3$CN/40% H$_2$O at 40 ml/min. Fractions were then eluted with a solution of 60% CH$_3$CN/40% 0.5N H$_2$SO$_4$, collecting an initial 1000 ml fraction followed by 500 ml fractions thereafter. Fractions 4–10 were pooled to a total volume of 3500 ml, the pH of which was 1.77. One liter of H$_2$O was added and the solution was extracted with 4000 ml of CH$_2$Cl$_2$. The CH$_2$Cl$_2$ layer was dried over anhydrous Na$_2$SO$_4$ and concentrated to dryness in vacuo to yield about 81 g of a brown oil.

Two portions of this oil, 12.5 gm and 50 gm respectively, were subjected to preparative reverse phase chromatography using a Sep Tech Model 800A preparative liquid chromatography with a 4 liter reverse phase C18 column. The chromatographic conditions for the two runs were as follows:

| 12.5 gm run | | | 50 gm run | | |
|---|---|---|---|---|---|
| Time (min) | % A | % B | Time (min) | % A | % B |
| 0 | 50 | 50 | 0 | 65 | 35 |
| 8 | 50 | 50 | 12 | 65 | 35 |
| 48 | 20 | 80 | 92 | 10 | 90 |
| 120 | 20 | 80 | 180 | 10 | 90 |
| Flow rate: 20 ml/min | | | Flow rate: 250 ml/min | | |
| Fraction size: ca. 810 ml | | | Fraction size: 1500 ml | | |
| Linear gradient between 8 and 40 min. | | | Linear gradient between 12 and 92 min. | | |

A = 0.1% $H_3PO_4$
B = acetonitrile

Fraction 13 from the 12.5 gm run and Fraction 14 from the 50 gm run were combined.

One liter of 10% NaCl, 0.1% HCl and 1.5 liter $CH_2Cl_2$ were added, mixed and the organic layer (3.1 liter) separated, dried over $Na_2SO_4$ and concentrated to yield ca 500 mg of residue.

The residue from above was dissolved in 4.5 ml 35:65 0.1% $H_3PO_4$-acetonitrile to give 4.7 ml of solution. A 4.5 ml aliquot of this solution was subjected to preparative reverse phase chromatography on a Rainin Dynamax-60A 8 λM C18 21.4 Mm ID×25 cm length column with a 21.4 Mm ID×5 cm length guard column of the same material. The eluent used was 35:65 0.1% $H_3PO_4$-acetonitrile at 10 ml/min and ambient temperature. Fractions of 10 ml were collected. Fractions 12–18 were combined, diluted with 150 ml 10% NaCl-0.1% HCl and extracted with 400 ml methylene chloride. After drying over anhydrous $Na_2SO_4$, the organic layer was concentrated to yield 470 mg residue.

This residue was taken up in 3 ml 40:60 0.1% $H_3PO_4$-acetonitrile and charged to the 21.4 mm ID column and guard column combination used above and eluted for 10 minutes with 45:55 0.1% $H_3PO_4$-acetonitrile at 10 ml/min and then with 40:60 0.1% $H_3PO_4$acetonitrile at ml/min. Fractions of 10 ml were collected. Fractions 31 to 41 were combined and diluted with 120 ml 10% NaCl-0.1% HCl. The resultant mixture was saturated with NaCl causing the separation of an aqueous layer and an organic layer (ca 50 ml).

Concentration of half of the organic layer yielded 87 mg of an oily residue. Three portions each containing 20% of the above material were separately subjected to preparative HPLC on a Rainin Microsorb 5 μm C18 10 mm ID×25 cm lenth with a 10 mm ID×5 cm length guard column of the same material. The eluent used was 42:58 0.1% $H_3PO_4$-acetonitrile at 4 ml/min. Fractions of 2 ml volume were collected. Fractions from the three portions were pooled based on results from analytical HPLC specifically, Fractions 45–47 from the first portion, Fractions 51–55 from the second portion and Fractions 54 to 57 from the third portion were combined. The combined fractions were diluted with 10% NaCl, 0.1% HCl and extracted with methylene chloride. The organic phase was dried with $Na_2SO_4$ and the solvent was removed yielding 18 mg of an oily residue. The 18 mg was freeze dried out of 1.5 ml benzene to yield 17.1 mg of a powdered material identified as compound A.

Physical Properties of Compound A

HPLC Analysis

Analytical HPLC of samples containing compound A was performed using a Microsorb C18 5 μm 4.6 mm ID×250 mm length column equipped with a 4.6 mm ID×15 mm length guard column of the same material (Rainin Instrument Co., Woburn, Mass.), eluent of 35:65 0.1% $H_3PO_4$: acetonitrile at 1 ml/min. The column was thermostated at 40° C. using a water jacket and a circulating water bath. The effluent was monitored at 210 nm. Under these conditions, Compound A eluted at about 12.7 minutes.

$^1$H-NMR Data (300 MHz, $CH_3OD$ referenced to solvent peak)δ 0.85 (d, 6.0, 3H), 0.86 (t, 3H), 0.87 (d, 6.8, 3H), 1.02 (d, 7.0, 3H), 1.13 (m, 2H), 1.25–1.45 (m, 3H), 1.95 (dd, 2.1, 15.3, 1H), 2.10 (s, acetate, 3H), 2.05–2.25 (m, 3H), 2.30 (m, 2H), 2.45 (m, 2H), 2.67 (dd, 6.2, 13.4, 1H), 2.85 (dd, 7.1, 15.3, 1H), 4.88 (s, 1H), 4.98 (s, 1H), 5.03 (s, 1H), 5.08 (d, 4.3, 1H), 5.77 (dd, 1.2, 15.3, 1H), 6.45 (dd, 2.0, 7.0, 1H), 6.82 (dd, 8.4, 15.5, 1H), 7.12–7.30 (m, 5H).

$^{13}$C-NMR Data of Compound A (75 MHz, $CH_3OD$)δ 11.54, 14.29, 19.30, 20.62, 20.98, 27.35, 30,87, 33.21, 35.63, 36.22, 37.99, 41.00, 42.56, 44.46, 74.64, 75.40, 76.35, 79.84, 92.96, 109.14, 111.98, 120.05, 127.05, 129.42(2), 130.23(2), 141.69, 147.58, 157.46, 166.65, 168.65, 170.10, 172.07, 172.68.

Mass Spectral Data Mass spectra were recorded on a Finnigan-MAT model TSQ70B mass spectrometer: Electron Impact (EI) 70eV; Fast Atom Bombardment (FAB) using as matrices 5:1 dithiothreitol/dithioerythritol (DTT/DTE) and glycerol for positive ion and negative ion modes, respectively. The FAB mass spectra indicated a MW 674 major component: observed $(674+Na)^+$ at m/z 697 and $[674-H]^-$ at m/z 673. The EI mass spectrum was weak, however $[M-AcOH]^+$ at m/z 614 and $[M-C_7H_7]^+$ at m/z 583 could be discerned.

EXAMPLE 2

As a specific embodiment of an oral composition of a compound of this invention, 20 mg of the compound from Example 1 is formulated with sufficient finely divided lactose to provide a total amount of 580 to 590 mg to fill a size 0 hard gelatin capsule.

EXAMPLE 3

Preparation of an Ammonium Salt

A 0.1 mmol sample of the free acid of Compound (I) is dissolved in 10 ml of ethyl acetate. The resulting solution is saturated with gaseous ammonia, upon which the ammonium salt precipitates from solution.

EXAMPLE 4

Preparation of Potassium Salt

A solution of 0.1 mmol of the free acid of Compound (I) in 10 ml of methanol is treated with an aqueous or methanolic solution containing 0.3 mmol of potassium hydroxide. Evaporation of the solvent affords the tripotassium salt. Addition of between 0.1 and 0.3 mmol of potassium hydroxide yields analogously mixtures of the mono-potassium, di-potassium and tri-potassium salts whose composition depends upon the exact amount of potassium hydroxide added.

In a similar fashion, the sodium and lithium salts of Compound (I) can be formed.

EXAMPLE 5

Preparation of a Calcium Salt

A solution of 0.1 mmol of the free acid of a compound of formula (I) in 20 ml of 6:4 methanol/water is treated with an aqueous solution of 0.1 mmol of calcium hydroxide. The solvents are evaporated to give the corresponding calcium salt.

EXAMPLE 6

Preparation of an Ethylenediamine Salt

A solution of 0.1 mmol of the free acid of a compound of formula (I) in 10 ml of methanol is treated with 0.1 mmol of ethylenediamine. Evaporation of the solvent affords the ethylenediamine salt.

The procedure can also be applied to the preparation of the N,N"-dibenzylethylenediamine salt.

EXAMPLE 7

Preparation of a Tris(hydroxymethyl)aminomethane salt

To a solution of 0.1 mmol of the free acid of a Compound of formula (I) in 10 ml of methanol is added from 0.1 to 0.3 mmol of tris(hydroxy-methyl)aminomethane dissolved in 10 ml of methanol. Evaporation of the solvent gives a corresponding salt form of Compound (I), the exact composition of which is determined by the molar ratio of amine added.

The method can also be applied to other amines such as, but not limited to: diethanolamine and diethylamine.

EXAMPLE 8

The preparation of a L-arginine salt

To a solution of 0.1 mmol of the free acid of a compound of formula (I) in 10 ml of 6:4 methanol/water is treated with an aqueous solution of 0.1-0.3 mmol of L-arginine. Evaporation of the solvent affords the title salt, the exact Composition of which is determined by the molar ratio of amino acid to the free acid of Compound (I).

Similarly prepared are the salts of L-ornithine, L-lysine, and N-methylglucamine.

EXAMPLE 9

Preparation of a Trimethyl Ester of Compound A

A solution of 2 mg of Compound A in 0.5 ml of acetonitrile is treated at room temperature with 10 equivalents of DBU and 10 equivalents of MeI. After 2 hours the reaction is diluted with 10 ml of dichloromethane and washed successively with 10 ml of 0.1 M phosphoric acid, 10 ml of water, 10 ml of saturated sodium bicarbonate and 10 ml of water. After drying over sodium sulfate, the organic layer is concentrated and the residue is chromatographed on silica gel using mixtures of hexane and ethyl acetate to give Compound B.

The method of Example 9 is also suitable for the preparation of other ester derivatives such as 1)ethyl and another lower alkyl esters and 2)benzyl and substituted benzyl esters.

What is claimed is:

1. A compound of structural formula (I)

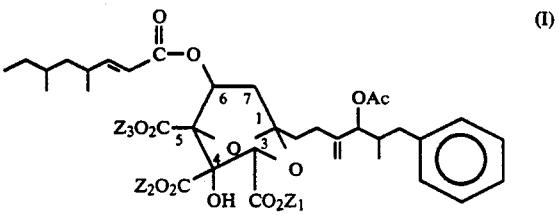

wherein
$Z_1$, $Z_2$ and $Z_3$ are each independently selected from;
a) H;
b) $C_{1-5}$alkyl; and
$C_{1-5}$alkyl substituted with a member of the group consisting of:
   i) phenyl, and
   ii) phenyl substituted with methyl, methoxy, halogen (Cl, Br, I, F) or hydroxy; or
a pharmaceutically acceptable salt of a compound of of formula (I).

2. A compound of claim 1 wherein structural formula (I) is:

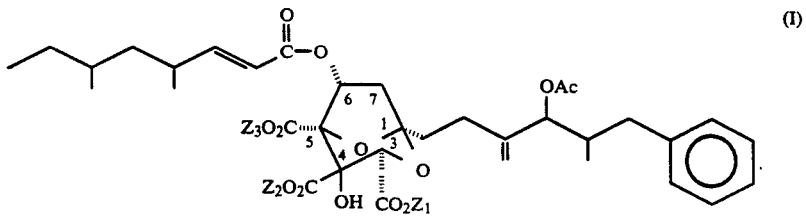

3. A compound of claim 2 wherein structural formula (I) is

4. A compound of claim 3 wherein structural formula (I) is:

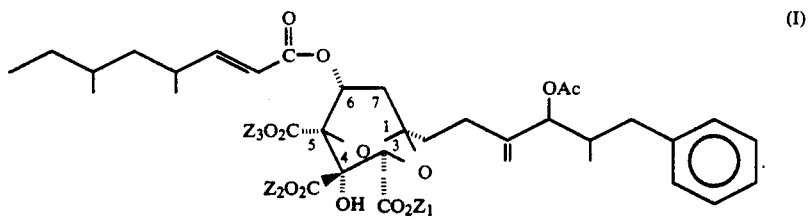

(I)

5. A compound of claim 4 wherein $Z_1$, $Z_2$ and $Z_3$ are each hydrogen or a pharmaceutically acceptable salt thereof.

6. A compound of molecular formula $C_{35}H_{46}O_{13}$ and molecular weight 674 characterized by the
   (a) $^{13}$C-NMR chemical shifts as measured in CH$_3$OD)δ 11.54, 14.29, 19.30, 20.62, 20.98, 27.35, 30.87, 33.21, 35.63, 36.22, 37.99, 41.00, 42.56, 44.46, 74.64, 75.40, 76.35, 79.84, 92.96, 109.14, 111.98, 120.05, 127.05, 129.42(2), 130.23(2), 141.69, 147.58, 157.46, 166.65, 168.65, 170.10, 172.07, 172.68 and
   (b) $^1$H NMR Chemical Shifts as measured in CD$_3$OD: δ 0.85 (d, 6.0, 3H), 0.86 (t, 3H), 0.87 (d, 6.8, 3H), 1.02 (d, 7.0, 3H), 1.13 (m, 2H), 1.25–1.45 (m, 3H), 1.95 (dd, 2.1, 15.3, 1H), 2.10 (s, acetate, 3H), 2.05–2.25 (m, 3H), 2.30 (m, 2H), 2.45 (m, 2H), 2.67 (dd, 6.2, 13.4, 1H), 2.85 (dd, 7.1, 15.3, 1H), 4.88 (s, 1H), 4.98 (s, 1H), 5.03 (s, 1H), 5.08 (d, 4.3, 1H), 5.77 (dd, 1.2, 15.3, 1H), 6.45 (dd, 2.0, 7.0, 1H), 6.82 (dd, 8.4, 15.5, 1H), 7.12–7.30 (m, 5H).

7. A pharmaceutical composition comprising a nontoxic therapeutically effective amount of a compound of claim 1 and a pharmaceutically acceptable carrier.

8. A pharmaceutical composition comprising a nontoxic therapeutically effective amount of a compound of claim 1 in combination with a pharmaceutically acceptable nontoxic cationic polymer capable of binding bile acids in a non-reabsorbable form in the gastrointestinal tract and pharmaceutically acceptable carrier.

9. A pharmaceutical composition comprising a nontoxic therapeutically effective amount of a compound of claim 1 in combination with a nontoxic therapeutically effective amount of a cholesterol lowering agent selected from the group consisting of:
   (a) HMG-CoA reductase inhibitor;
   (b) HMG-CoA synthase inhibitor;
   (c) Squalene expoxidase inhibitor;
   (d) Probucol;
   (e) Niacin;
   (f) Gemfibrozil; and
   (g) Clofibrate.

10. A composition of claim 9 wherein the cholesterol lowering agent is an HMG-CoA reductase inhibitor.

11. A composition of claim 10 wherein the HMG-CoA reductase inhibitor is selected from lovastatin, simvastatin, pravastatin and fluvastatin.

12. A method of treating hypercholesterolemia comprising the administration to a subject in need of such treatment a nontoxic therapeutically effective amount of the compound of claim 1.

13. A method of inhibiting squalene synthetase comprising the administration to a subject in need of such treatment a nontoxic therapeutically effective amount of a compound of claim 1.

14. A method for inhibiting fungal growth comprising applying to the area where growth is to be controlled an anti-fungally effective amount of a compound of claim 1.

15. A method for inhibiting fungal growth comprising applying to the area where growth is to be controlled an anti-fungally effective amount of a compound of claim 5.

* * * * *